US006225354B1

(12) United States Patent
Perez

(10) Patent No.: US 6,225,354 B1
(45) Date of Patent: May 1, 2001

(54) HIGH MOLECULAR WEIGHT PRIMARY ALIPHATIC ALCOHOLS OBTAINED FROM BEESWAX AND PHARMACEUTICAL USE THEREOF

(75) Inventor: Pedro P. Perez, Miami, FL (US)

(73) Assignee: Cholesterol Control Laboratories, Inc., Ft. Lauderdale, FL (US)

( * ) Notice: Subject to any disclaimer, the term of this patent is extended or adjusted under 35 U.S.C. 154(b) by 0 days.

(21) Appl. No.: 09/337,339

(22) Filed: Jun. 21, 1999

(51) Int. Cl.[7] .................. A61K 31/045; C07C 29/76; C07C 29/86
(52) U.S. Cl. .................. 514/724; 514/164; 568/840; 568/913; 568/918
(58) Field of Search .................. 514/164, 724; 568/840, 913, 918

(56) References Cited

U.S. PATENT DOCUMENTS

| | | |
|---|---|---|
| 3,031,376 | 4/1962 | Levin et al. |
| 4,623,667 | 11/1986 | Gans et al. |
| 4,793,991 | 12/1988 | Slimak |
| 5,166,219 | * 11/1992 | Katz ..................... 514/724 |
| 5,663,156 | 9/1997 | Granja et al. |
| 5,856,316 | 1/1999 | Granja et al. |

FOREIGN PATENT DOCUMENTS 0 654 262    5/1995   (EP).

OTHER PUBLICATIONS

Schmid, Natarajan V., "1–Docosanol and other long chain primary alcohols in developing rat brain"; Lipids 1977 Jan; 12(1): 128–30.

Kellsak, Borg J., et al., "Peripheral administration of a long–chain fatty alcohol promotes septal cholinergic neurons survival after fimbria–fornix Transection"; Brain Res Jun. 1990 4:518(1–2);295–8.

Liu, F., et al. "Active constituents lowering blood–lipid in beeswax"; Chung Kuo Chung Yao Tsa Chih Sep.1996; 21(9): 553–4, 576.

H. Sho, et al., "Effects of okinawan sugar cane wax and fatty alcohol on serum and liver lipids in the rat"; J Nutr Sci Vitaminol (Tokyo) Dec. 1984; 30(6): 553–9.

Karino, et al., "Octacosanol affects lipid metabolism in rats fed on a high–fat diet"; Br J. Nutr 1995 Mar;73(3): 433–41.

Kabiry et al., Tissue distribution of (8–14C)–octacosanol in liver and muscle of rats after serial administration; Ann Nutr Metab 1995;39(5):279–84.

Azzouz M. et al., "Enhancement of mouse sciatic nerve regeneration by the long chain fatty alcohol, n–hexacosanol", Exp Neurol Apr.1996; 138(2):189–97.

Borg, J., The Neurotrophic Factor, n–hexacosanol, reduces the neuronal damage induced by the neurotoxin, kainic acid; J Neurosci Res May 1991;29(1):62–7.

Kabir et al., "Distribution of radioactive octacosanol in response to exercise in rats", Nahrung 1994;38(4):373–7.

Warren RP, et al., "Effect of triacontanol on numbers and functions of cells involved in inflammatory responses", Proc Soc Exp Biol Med Jul. 1992; 200(3):349–52.

* cited by examiner

*Primary Examiner*—Peter O'Sullivan
(74) *Attorney, Agent, or Firm*—Blank Rome Comisky & McCauley, LLP

(57) ABSTRACT

The present invention relates to a naturally obtained mixture of higher molecular weight primary aliphatic alcohols which contain 24 to 34 carbon atoms. This invention also relates to the process for obtaining the alcohol mixture by extraction and purification with organic solvents from beeswax without saponification ofthe beeswax. The alcohol mixture obtained from beeswax has enhanced purity and contains a mixture of alcohols having 24, 26, 27, 28, 29, 30, 32 and 34 carbon atoms. The alcohol mixture is useful in pharmaceutical compositions, foodstuffs and dietary supplements and is effective for lowering cholesterol in LDL-C levels so that it is effective in treating hypercholesterolemia. Consequently the composition may be used to reduce the risk of coronary heart disease, the atherosclerotic process (platelet hyperaggregability, ischemia and thrombosis) and also acts as an anti-inflammatory and anti-thrombotic agent. The composition also possesses neurotrophic properties and is useful for improving male sexual activity.

19 Claims, No Drawings

HIGH MOLECULAR WEIGHT PRIMARY ALIPHATIC ALCOHOLS OBTAINED FROM BEESWAX AND PHARMACEUTICAL USE THEREOF

BACKGROUND OF THE INVENTION

1. Field of the Invention

The present invention pertains to a pharmaceutically active mixture of primary high molecular weight aliphatic alcohols having enhanced purity which is isolated from beeswax. More particularly the invention pertains to a highly pure mixture of primary aliphatic alcohols which are naturally obtained from beeswax by liquid extraction from the solid wax without saponification wherein the alcohols in the mixture contain 24 to 34 carbon atoms. The $C_{24}$–$C_{34}$ alcohols in the mixture advantageously consist of straight chain alcohols having 24, 26, 27, 28, 29, 30, 32 and 34 (i.e., tetracosanol, hexacosanol, heptacosanol, octacosanol, nonacosanol, triacontanol, dotriacontanol and tetratriacontanol). The invention also pertains to the method of extracting the aforementioned mixture from selected beeswax by a solid-liquid extraction procedure without saponification. The invention also pertains to the pharmaceutical use of the mixture and pharmaceutical compositions, foodstuffs and dietary supplements for administering the composition.

2. Background Information

All kinds of waxes, and more especially beeswax, have always been a matter of interest. This has been the case not only because of their industrial application, but also because of their chemical composition. The amount of beeswax in honey ranges between 0.9% to 1.13%, depending on the methods used to separate the wax from the honey. This wax is made up of monesters, hydrocarbons, free fatty acids and free alcohols.

The natural mixture of straight chain aliphatic alcohols obtained from beeswax has been studied by several authors to learn about its composition and main features. The obtaining of different groups of mixtures from all kinds of waxes has been reported in previous studies. (J. A. Lamberton et al., 1959, Australian Journal of Chemistry 13,261–268 and A. Horn and J. S. Martic, 1957 Journal of Science Food and Agriculture 10,571) and (Kreger, 1948; Wimbero, 1904; Mitsui and Col 1842). These studies suggest a method for obtaining fatty alcohols based on the homogeneous saponification with alcoholic potassium hydroxide, followed by the esterification of the unsaponifiable material and further molecular distillation.

Another method also reported is extraction of the natural alcohol mixture through a high efficiency high vacuum. The high vacuum wax distillation for the chemical isolation of carbonylic mixture derivatives and the extraction of the remaining wax is done by using petrol ether. The solvent evaporates and the remaining content is acetylated for its further isolation through alumina chromatography. Finally, through alkaline hydrolysis, alcohols are obtained and then recrystallized in ethanol, showing a fusion point ranging from 79 to 83 degrees Celsius.

Blood-lipid lowering effects of a natural mixture of straight chain aliphatic alcohols have been demonstrated by several authors (F. Liu, 1996 Active Constituents lowering blood-lipid in bees wax; Chung Kor. Chung Yao Tsa Chih 21 (9) 553–4, 576); (H. Sho et al. 1984, Effects of Okinawa sugar cane wax and fatty alcohols on serum and liver lipids in the rats; J. Nutri Vitaminol 30(6) 553–559); (S. Kato, K. Hamatani et al., 1995, Octacosanol Effects lipid metabolism in rat fed on a high fat diet; Br J Nutr 73(3) 433–441); (Kabiry et al. 1995, Tissue distribution of 8–14c) octacosanol in liver and muscle of rats after serial administration; Ann Nutr Metab 39(5) 279–284). Many investigational studies based on clinical studies with the use of the natural mixture of straight chain aliphatic alcohols have been published.

These studies have demonstrated the characteristics associated with ergogenic effects in humans and animals as well as benefits in the cardiovascular, cerebral and muscular systems. Other studies have reported that these alcohols also stimulate growth in plants-(V. Natarajan, H. H. Schmid 1997 1 -Docosanol and Other long chain primary alcohols in developing rat brain, Lipids 12(1) 128–130) (M. Azzouz, J. Borg, 1996, Enhancement of mouse sciatic nerve regeneration by the long chain fatty alcohol, N-hexacosanol, Exp Neurol 138(2) 189–197) (J. Borg, 1991 The neurotrophic Factor, n-hexacosanol, reduces the neuronal damage induced by the neurotoxin, kainic acid; J Neurosci Res (29)(1) 62–67) (J. Borg, P. J. Kesslak, C. W. Cotman, 1990, Peripheral administration of a long chain fatty alcohol promotes septal cholinergic neurons survival after fimbria fornix transection; 4; 518 (1–2)295–298) (Y. Kabir, S. Kimura 1994, Distribution of radioactive octacosanol in response to exercise in rats; 38 (4) 373–377) (R. P. Warren, R. A. Burger, R. W. Sidwell, L. L. Clark, 1992, Effect of triacontanol on numbers and functions of cells involved in inflammatory responses, 200(3)349–352) P. W. Westerman, J. M. Pope, N. Phonphok, J. W. Dan, D. W. Dubro, Biochim Biophys Acta (NETHERLANDS) 939, 64–78 (1988). Studies have been conducted regarding the partitioning of long-chain alcohols into lipid bilayers. In U.S. Pat. No. 3,031,376, Ezra Levin reported that tetracosanol, hexacosanol, octacosanol and triacontanol and their esters improved physical performance of athletes and disclosed compositions comprising such alcohols and esters in vegetable oil bases for oral ingestion. Various constituents of beeswax and products derived from beeswax have also been used in cosmetic and therapeutic applications, as disclosed by Karen M. Slimak in U.S. Pat. No. 4,793,991 which describes a hypoallergenic cosmetic comprising single plant source beeswax. Gans et al. have described the use of the non-polar saturated straight chain $C_{21}$ to $C_{33}$ hydrocarbon fraction of beeswax in the treatment of inflammatory skin disorders in U.S. Pat. No. 4,623,667.

A procedure for obtaining a natural mixture of straight chain higher aliphatic primary alcohols from animal and vegetable wax (a natural source wax) is also known in the prior art. This prior art procedure is based on the extraction of alcohol mixtures with fluid extractant in the sub and supercritical states between 20 and 100 degrees Celsius. Selective extraction can be carried out with this procedure but when this is applied to beeswax it is only possible to obtain 7% of $C_{24}$ to $C_{34}$ alcohol mixture.

Other projects (S. Inaa, K. Furukama, T. Masui, K. Honda, J. Ogasawara, and G. Tsubikamoto, 1986; Process for recovering primary normal aliphatic higher alcohols JP 60-119514) proposed a very similar extraction method applied to waxes that is based on fluids ($CO_2$ with ethylene) in sub and supercritical states.

There are different commercial dietary supplements, foods and drugs to aid in the lowering of total blood cholesterol (lowering lipid, LDL and cholesterol levels) which are considered as effective, safe and well tolerated but most of them produce different adverse side effects. Since lipid-lowering therapy must be chronically administered, safety and tolerableness are very important for their definitive acceptance. Although many products from different sources exist in the market such as Sitosterol, garlic, bile acid binders, fibric acid derivatives, HMG-Co A reductos and Nictoinic acid, etc., the methods of use and the quantities necessary of these products are not sufficiently effective for the reduction of cholesterol to the desired levels. In addition, the drugs that are used for the lowering of cholesterol have several adverse side effects.

It has been described that treatment with some lipid-lowering drugs reduces the tendency for platelet hyperaggregation frequently seen in the hyperlipidemic patients and experimental data has shown anti-aggregatory effects mediated by these compounds. Nevertheless, only some cholesterol-lowering drugs show this property. Atherosclerosis is a variable combination of changes of the intima of the arteries consisting of the focal accumulation of lipids, complex carbohydrates, blood and blood products, fibrous tissue and calcium deposits, frequently also associated with medial changes. Thus, atherosclerosis is known as multifactorial process and includes hyperlipidemia as a risk factor.

Among the factors contributing to atherosclerosis development, platelet aggregation has a very important place. Platelet releasing granule contents activate arachidonic acid, which metabolizes into cyclic endoperoxides. These are mainly transformed into cyclic endoperoxides and finally rendering thromboxane A2 (TxA2), a strong vascular vasoconstrictor and platelet aggregatory agent. Platelet aggregation can be elicited by numerous compounds, such as collagen, ADP and epinephrine. Thus, different experimental "in vivo", "ex vivo", or "in vitro" models testing effectiveness of putative antiplatelet drugs commonly test their effect on platelet aggregation induced by these agents.

These tests are also used for testing platelet aggregation in healthy volunteers and in patients with disease which induces hyperaggregability such as hypercholesterolemia and diabetes. Collagen-induced platelet aggregation is one of the most frequently used tests. Thus, for example, collagen injected endovenously leads to reversible intravascular platelet aggregation "in vivo" and aggregates of platelet enter the vascular microcirculation, subsequently decreasing the count of circulating platelet and simultaneously increasing the plasma MDA concentration. Moreover, in some species this injection of collagen induces mortality produced by thrombosis. In these models, antiplatelet drugs generally prevent the decrease platelet content and increase of MDA concentration, as well as collagen induced mortality.

Some drugs showing platelet anti-aggregatory effects are useful for treatment of thrombotic diseases, myocardial infarction and stroke, but not all show these advantages. On the other hand, there are antithrombotic drugs such as estreptokinase and urokinase that mainly act by lytic processes affecting blood coagulation, but not on the platelet aggregation.

Since ischemic cardiovascular diseases, stroke and vascular peripheric obstructive pathologies are the main sequelae of atherosclerosis, effects of several drugs on these complications are commonly tested. Thus, theoretically a drug showing cholesterol lowering properties that also can prevent these complications by acting on other events involved in these processes must be advantageous for treating these patients. Likewise, reduction of TxA2 levels have been associated not only with antiplatelet and antithrombotic effects, but also with antischemic effects.

The pharmacological screening of antischemic drugs commonly includes the evaluation of their effects on brain-induced global ischemia. Thus, the protective effect of different drugs on rat cerebral ischemia has been determined by this type of evaluation for certain non-steroidal anti-inflammatory drugs (NSAID) which inhibits reactions catalyzed by cyclooxygenase, as well as for specific inhibitors of thromboxane synthetase and prostacyclin ($PgI_2$) analogues (M. G. Borzeix and J. Cahn, 1988; Effects of new chemically metabolically stable prostacyclin analogues on early consequences of a transient cerebral oligemia in rats; Prostaglandins 35,5, 653–664). Other experimental models, such as global ischemia induced experimentally in Mongolian gerbils are also used frequently.

Acetylsalicylic acid (ASA) is a compound exhibiting antiplatelet, antithrombotic and antischemic properties in experimental models and human beings. It is the drug most widely used for treatment of acute myocardial infarction and stroke as well as for prevention of thromboembolic disorders. ASA effects are supported by its well known inhibition of cyclooxygenase, a key enzyme on the arachidonic acid metabolism. Thus, ASA induces a significant and remarkable reduction of serum levels of thromboxane A2 (TxA2) a recognized pathophysiological agent for the vascular endothelium and it explains the aforementioned effects of ASA.

U.S. Pat. No. 5,633,156 describes a mixture of $C_{24}$–$C_{34}$ higher primary aliphatic alcohols obtained from sugar cane wax. The alcohol mixture obtained from sugar cane wax (referred to the '156 patent as MHPAA) has the same pharmaceutical utility as the beeswax mixture of higher primary aliphatic alcohols of the present invention (referred to hereinafter as BMHPAA) and can therefore be used and administered in the same manner as described in the '156 patent. However the MHPAA of the '156 patent can only be obtained by saponification of the sugar cane wax (an ester) with harsh alkali in order to obtain sufficient alcohol because sugar cane wax does not contain sufficient free alcohol to obtain a sufficient recovery of the desired alcohol product. Thus the products of saponification (i.e., alkali metal salts of the high molecular weight carboxylic acids) are formed in the material from which the alcohols must be isolated and recovered. The presence of such salts obviously poses an obstacle to the purification and recovery of the desired $C_{24}$–$C_{34}$ alcohols. Furthermore, alcohols obtained from sugar cane wax, being formed by means of a chemical reaction (saponification) are not naturally derived from the wax. The term "naturally derived alcohols" as used in the present invention therefore means that the alcohols are recovered and isolated from the wax without chemical reaction with a precursor compound. In the '156 patent the alcohols are obtained by saponification of the ester precursor compounds which are naturally contained in the wax.

SUMMARY OF THE INVENTION

It is an objective of this invention to provide a mixture of higher primary aliphatic alcohols having an enhanced level of purity without the need to saponify the ester wax from which the alcohols are obtained.

It is another objective of this invention to provide an improved extraction method for obtaining a highly pure mixture of higher primary aliphatic alcohols.

It is another objective of this invention to improve the purity level of a mixture of higher primary aliphatic alcohols which contain 1-tetracosanol, 1-hexacosanol, 1-heptacosanol, 1-octacosonal, 1-nonacosanol, 1-triacontanol, 1-dotriacontanol, and 1-tetratriacontanol therein.

It is another objective of this invention to improve the percent recovery of the aforementioned mixture of $C_{24}$–$C_{34}$ primary aliphatic alcohols obtained by solid-liquid extraction from naturally occurring ester wax.

It is another objective of this invention to provide a pharmaceutical composition which contains a highly pure mixture of $C_{24}$–$C_{34}$ primary aliphatic alcohols as an active ingredient by itself or in combination with other active ingredients.

It is another objective of this invention to provide an improved mixture of higher ($C_{24}$–$C_{34}$) primary aliphatic alcohols which has desired pharmaceutical properties including antiplatelet, anti-inflammatory, anti-thrombotic and antischemic properties; which is useful in the prevention of foam cell development; which is useful in the treatment of hypercholesterolemia; which provides an effective effect on the vascular endothelium; which can be used for the prevention of early atherosclerotic lesions (thrombus formation) and which demonstrates neurotrophic properties.

These and other objectives are obtained by extracting the desired mixture of higher ($C_{24}$–$C_{34}$) primary aliphatic alcohols from beeswax in a solid-liquid extraction procedure to obtain a highly pure mixture of alcohols (i.e., purified or isolated from the non-alcoholic components which naturally occur in the beeswax) which include $C_{24}$–$C_{34}$ primary aliphatic alcohols (i.e., 1-tetracosanol, 1-hexacosanol, 1-heptacosanol, 1-octacosonal, 1-nonacosanol, 1-triacontanol, 1-dotriacontanol, and 1-tetratriacontanol). Preferably the alcohols in the composition are limited to the aforementioned $C_{24}$–$C_{34}$ alcohols and thus the preferred alcohol mixture consists essentially of the aforementioned $C_{24}$–$C_{34}$ alcohols. As noted above, above, the alcoholic mixture obtained from beeswax in accordance with the present invention is referred to herein as BMHPAA to distinguish it from the MHPAA disclosed in U.S. Pat. No. 5,663,156. Also, as noted above, the BMHPAA of the present invention can be formulated in a pharmaceutical composition, foodstuff or dietary supplement and administered to humans and other animals as described in the '156 patent. Accordingly the specification of U.S. Pat. No. 5,663,156 is incorporated here in by reference in order to aid in an understanding of the present invention and its distinction over the aforementioned patent and to further illustrate how the composition of the present invention is administered and used to treat hypercholesterolemia and other conditions.

It has been discovered that the use of beeswax as the source of the alcohol mixture offers numerous benefits which cannot be obtained when sugar cane wax is used as the source. For example, many factors are associated with purity levels of sugar cane wax which are difficult to control and thus it is difficult to obtain a reliable source of sugar cane wax which meets the requirements for consistently obtaining a uniform pure product. In particular the purity level of sugar cane wax is influenced by the sugar cane variety, age of the plant, soil and climate conditions where the sugar cane is grown and the level and type of fertilizer used to grow the sugar cane. In addition the type of operational procedure used to extract the wax from the husk can influence the level of purity. None of these factors are significant when beeswax is used as the source for the alcohol mixture. Furthermore, minor variations in beeswax characteristics can be corrected by blending of selected waxes which meet certain criteria with respect to parameters as further described herein.

Furthermore, preferred levels of certain operational parameters in the extraction and purification process have been discovered which lead to further enhancement of the purity level of the isolated alcohols and enhanced percent recovery of the alcohols from the beeswax. These operational parameters include one or more of the following: particle size of the solid (i.e., the particle size of the beeswax), relationship between solid and liquid (i.e., solid:liquid ratio), temperature range, fluid regimen, crystallization regimen, centrifuge regimen and contact time. The preferred levels of these parameters were established under experimental design in the laboratory as well as at the pilot plant and industrial level.

The extraction of the beeswax may be performed through the use of conventional solid-liquid extraction procedures using the solids and solvents as described herein without any saponification being needed to obtain free alcohols in the material which is to undergo extraction. As noted above preferred levels of one or more of the operational parameters may be selected to further improve the purity and recovery of the alcohols. Thus the selection of beeswax and avoidance of a saponification step illustrates significant departures from the technology described in U.S. Pat. No. 5,666,156. Furthermore, the preferred levels of the aforementioned parameters serve to further distinguish the present invention from U.S. Pat. No. 5,666,156. For example the '156 patent performs recrystallization of the obtained wax at room temperature (i.e., about 20° C.–22° C.) wherein the present invention performs recrystallization at 2° C.–10° C.

The doses and method for administering the BMHPAA of this invention may be in accordance with the doses and administration of the MHPAA as set forth in U.S. Pat. No. 5,663,156.

Table 1 shows the qualitative and quantitative composition of the mixture of higher primary aliphatic alcohols obtained from beeswax according to the present invention.

TABLE 1

| Components | Percent by Weight in the Mixture |
| --- | --- |
| 1-tetracosanol | 1–4% |
| 1-hexacosanol | 7–12% |
| 1-heptacosanol | 1–4% |
| 1-octacosanol | 30–60% |
| 1-nonacosanol | 2–5% |
| 1-triacontanol | 16–26% |
| 1-dotriacontanol | 13–22% |
| 1-tetratriacontanol | 2–6% |

Table 2 shows the qualitative and quantitative composition of a preferred mixture of higher primary aliphatic alcohols obtained from beeswax according to the present invention.

TABLE 2

| Components | Percent by Weight in the Mixture |
| --- | --- |
| 1-tetracosanol | 2–4% |
| 1-hexacosanol | 9–10% |
| 1-heptacosanol | 2–3% |
| 1-octacosanol | 35–40% |
| 1-nonacosanol | 3–4% |
| 1-triacontanol | 19–22% |
| 1-dotriacontanol | 15–20% |
| 1-tetratriacontanol | 3–4% |

The composition of the invention has new surprising pharmaceutical properties including antiplatelet, anti-inflammatory, anti-thrombotic and antischemic properties. In addition the composition is useful in the prevention of foam cell development, the treatment of hypercholesterolemia; provides a protective effect on the vascular endothelium and can be used for the prevention of early atherosclerotic lesions (thrombus formation). The composition also demonstrates neurotrophic properties.

The optimal composition for the natural mixture of higher aliphatic primary alcohols of the present invention is described in Table 3.

TABLE 3

| Components | Percent by Weight in the Mixture |
| --- | --- |
| 1-tetracosanol | 3.5 ± 0.1% |
| 1-hexacosanol | 9.5 ± 0.2% |
| 1-heptacosanol | 2.0 ± 0.2% |
| 1-octacosanol | 38.5 ± 1.2% |
| 1-nonacosanol | 3.5 ± 0.1% |
| 1-triacontanol | 20.5 ± 0.6% |
| 1-dotriacontanol | 16.5 ± 0.4% |
| 1-tetratriacontanol | 3.5 ± 0.1% |

The Pharmaceutical composition, Foodstuffs, and Dietary Supplement formulated with the natural mixture of higher aliphatic primary alcohols of this invention may be administered to humans and animals. The daily dosage of this natural mixture obtained from beeswax to be used for the reduction and prevention of hyper-cholesterolemic diseases, cholesterol, coronary heart disease (heart attacks and stroke), inflammation or immunoregulatory diseases, cardiovascular disease and neurodegenerative disorders is established between 1 to 100 mg per day (preferably 3 to 20 mg) and is intended for ingestion in any type or form of food stuff, capsule, tablet or liquid form.

DETAILED DESCRIPTION OF INVENTION AND PREFERRED EMBODIMENTS

The procedure of the current invention is based on the extraction and purification of the natural mixture of straight chain aliphatic alcohols (higher aliphatic primary alcohols) from beeswax, preferably refined beeswax. The solid (beeswax) is subjected to liquid extraction in a solid-liquid extractor where the natural alcohols mixture is selectively extracted with adequate organic solvents. Adequate solvents include acetone, toluene, benzene, ethanol, heptane, methanol, phenol, ether, trichloroethane, methyl ethyl ketone, butanol, 1,2 dichloroethane, dichloromethane, chloroform and others). Mixtures of the above-identified solvents can also be used in the extraction process.

The extraction is carried out in periods ranging between 3 to 7 hours. Afterwards, the mixture is successively crystallized using the above-mentioned solvents or their mixtures. The yield (i.e., percent recovery by weight of alcohols with respect to the weight of the beeswax) attained ranges about 35% with purity ranges from 93 to 99%. The natural mixture obtained contains alcohols ranging from 24 to 34 carbon atoms, with amelting point between 72.5 and 78.5 degrees Celsius. The natural mixture of straight chain aliphatic alcohols obtained by this process may be analyzed through gas chromatography in Fused Silica Capillary Column using N-Methyl-N-trimethylsilyltrifluoroacetamide (MSTFA) as solvent to separate the alcohols. The procedure of this invention for obtaining the natural mixture of higher primary molecular weight aliphatic alcohols from beeswax has some advantages compared to other prior art procedures.

One of these advantages is related with the short obtention time. Other advantages of this invention are related to the practical yields (near 40% in weight) compared with the previously reported results with yields lower than 5%. Another advantage of the procedure relates to the purity that can be obtained (near 99%) which is significantly higher than the purity in the prior art methods. Thus, the method of the present invention is simple and appropriate for large scale production.

Finally, the highly pure mixture of primary aliphatic alcohols having 24–34 carbon atoms obtained from beeswax in accordance with the present invention has excellent safety, effectiveness and tolerableness which give it a significant advantage when compared with other supplements or drugs. Short and long term clinical trials also support the excellent safety and tolerableness of treatment with the composition of the invention.

The extraction of the alcohols from the beeswax may be performed in accordance with conventional solid-liquid extraction procedures which are well known to those skilled in the art. The preferred parameters are as follows:

|  | Range: | Optimal: |
| --- | --- | --- |
| Particle Size of Solid |  |  |
| Mesh, | 120–35 | 60 |
| mm, | 0.125–0.50 | 0.25 |
| Microns, | 125–500 | 250 |
| Solid and Liquid Relationship |  |  |
| Extraction | 1–4 to 1–8 | 1–6 |
| Purification | 1–6 to 1–14 | 1–10 |
| Temp. Range |  |  |
| Extraction | 50–60 C. | 56 C. |
| Purification | 60–70 C. | 56 C., 66 C. |
| Fluid Regimen |  |  |
|  | 40–100 RPMs | 80 RPMs |
| Crystallization Regimen |  |  |
| Extraction | RPMs 40–80 | 60 RPMs |
|  | Temp 2 C.–10 C. | 6 C. |
| Purification | RPMs 40–80 | 60 RPMs |
|  | Temp 2 C.–10 C. | 6 C. |
| Centrifuge Regimen |  |  |
|  | 80 RPMs–2000 RPMs | RPM program incrementing in speed over 2 hrs from 80 to to 2000 RPMs |
|  | Wash time 1–2 min |  |
| Contact Time |  |  |
| Extraction | 3–5 hrs | 4 hrs every extraction cycle |
| Purification | 1–2 hrs | 1.5 hrs |
| Crystallization | 1–3 hrs | When the crystallized mix reaches 6 C. |

The beeswax is preferably selected to meet certain quality control parameters in order to obtain a preferred enhanced level of purity and percent recovery obtained with this invention. These quality control parameters are summarized below in Table 4. Table 4 includes a listing of various laboratorytests and the corresponding specifications or tolerance limitations for each laboratory test. For example, the melting point of the wax should range between 61 through 65° C. and the cloud point should be less than 65° C. Table 4 also shows the actual results of a particular wax which has been tested to determine if it meets the quality control parameters established herein.

TABLE 4

| Laboratory Test | Specifications | Actual Results |
| --- | --- | --- |
| Melting Point | 61–65° C. | 62.0° C. |
| Cloud Point | <65° C. | 64° C. |
| Flash Point | 242–250° C. | 245.6° C. |
| Specific Gravity @ 25 C. | 0.950–0.960 | 0.955 |
| Saponification Value | 88–102 | 100 |
| Resin Value | 1–2 | 1.2 |
| Oil Value | 2–6 | 3.60 |
| Acid Value | 17–24 | 20.56 |
| Ester Value | 72–79 | 78.21 |
| Ester - Acid Ratio | 3.3–4.2 | 3.80 |
| Free Alcohol Value | 3–10 | 5.30 |

In view of the specifications or tolerances established above in FIG. 4, one can obtain various lots of beeswax which are commercially available and test them for each of the various criteria outlined in Table 4. Once the results of the tests are known for each lot of beeswax, one can then readily ascertain which of the various lots of beeswax are acceptable for blending into beeswax which is to be extracted in accordance with the present invention.

In a preferred embodiment the beeswax is ground to achieve a particle size of 125–500 microns in diameter, preferably 250 microns in diameter. The particles of wax are placed into a conventional solid-liquid extractor. An organic solvent extractant is also introduced into the extractor for contact with the particles of beeswax contained therein. Preferably acetone is used as the extractant. The ratio of beeswax particles to liquid extractant is preferably from 1:4 to 1:8, preferably 1:6. The extraction is conducted for 3 to 5 hours, preferably 4 hours within a temperature range of 50°–60° C., preferably 56° C. The beeswax particles are preferably agitated during the extraction procedure, for example by use of a rotating agitator to agitate the particles while in contact with the solvent. Advantageously the agitator is rotated at 40–100 rpm, preferably 80 rpm. During the extraction procedure the alcohols become solubilized in the extractant thus producing a wax residue. Upon completion of the extraction, the extractant containing the alcohols dissolved therein is removed from the waxy residue.

Next the extractant containing the alcohols dissolved therein, is introduced into a chamber for crystallizing the alcohols. The alcohols are advantageously crystallized by reducing the temperature of the extractant in the crystallizer to form crystals of the alcohols in the extractant (e.g., an alcohol-extractant suspension or mixture). Preferably the temperature in the crystallizer should be uniform. An agitator may be provided within the crystallizer to assure a uniform temperature therein. Preferably the agitator is rotated at 40–80 rpm, preferably 60 rpm. The temperature during crystallization is maintained within the range of 2°–10° C., preferably 6° C.

The suspension or mixture obtained from the crystallizer is then centrifuged to recover solid alcohol crystals. Preferably centrifugation takes place by initially centrifuging the mixture or suspension at 80 rpm and gradually increasing the revolutions per minute to 2,000 rpm over a 2 hour period of time. During centrifugation the particles of alcohol may be washed with a spray of clean extractant for about 1–2 minutes to remove contaminating material which may be contained in the extractant.

The clean solid alcohol mixture obtained from the centrifugation step is then sent to a purifier where it is contacted with another solvent which is preferably hexane. The alcohol crystals are dissolved in the hexane to form an alcohol-hexane solution. The hexane-alcohol solution is then introduced into a crystallizer for recrystallization. The recrystallization is performed under the same conditions as the initial crystallization of the alcohols from the acetone solution. Thus the same type of crystallizer maybe used in the recrystallization step as was used in the initial crystallization of alcohol from the acetone. The temperature of the hexane-alcohol solution is kept uniform preferably by agitating with an agitator at 40–80 rpm, preferably 60 rpm. The temperature during recrystallization is maintained at 2°–10° C., preferably 6° C. The recrystallization step forms a mixture or suspension of alcohol crystals in the hexane solvent.

The suspension or mixture of alcohol crystals in the hexane is then introduced into a centrifuge where it is centrifuged in the same manner that the solid alcohol suspension or mixture was centrifuged from the acetone solvent. During this second centrifugation step, the alcohol crystals are washed for 1–2 minutes with a spray of clean solvent (hexane).

The washed particles obtained from the second centrifugation step are then recovered and dried. Vacuum drying may be used. A pressure of 400 millibars at a temperature of 31° C. may be used during the vacuum drying step.

After the particles are dried, they are then ready to be formulated into a conventional pharmaceutical formulation such as tablets, capsules, etc., for administration.

The below-described examples further describe the invention and preferred embodiments thereof.

EXAMPLE 1

(1 kg) of solid (beeswax) is extracted in a conventional solid-liquid extraction system a ratio (solid to liquid) of 1 to 50 for 10 hours using methanol as solvent. The extract obtained was cooled at temperatures ranging from 2 degrees C. to 15 degrees C., whereby a mixture of $C_{24}$–$C_{34}$ primary aliphatic alcohols was crystallized and recovered. The crystallized mixture of alcohols was then recrystallized in chloroform within a temperature range of from 2 degrees C. to 10 degrees C. 325 g of the recrystallized alcohol mixture was obtained with a purity amounting to 95.47%. The melting point of the recovered natural alcohol mixture ranges from 72.5 degrees C. to 75.5 degrees C. The qualitative and quantitative composition of the recovered recrystallized mixture is shown in Table 4A.

TABLE 4A

| Alcohol | Percent by Weight in the Mixture |
| --- | --- |
| 1-tetracosanol | 3.49 |
| 1-hexacosanol | 9.30 |
| 1-heptacosanol | 1.81 |
| 1-octacosanol | 37.39 |
| 1-nonacosanol | 3.43 |
| 1-triacontanol | 19.99 |
| 1-dotriacontanol | 16.66 |
| 1-tetratriacontanol | 3.40 |

EXAMPLE 2

(2 kg) of solid (beeswax) was subjected to liquid extraction in a solid-liquid extraction system with a solid to liquid ratio of 1 to 100 for 8 hours using toluene as solvent. The obtained extract was left to cool at a temperature range of 2 degrees C. to 15 degrees C., and the solid obtained was recrystallized in a mixture of butanol and chloroform (1:1), in a temperature range of 2 degrees C. to 10 degrees C. The natural alcohols mixture (610 g) which was obtained had a purity of 95.93%. The melting point ranges from 72.7 degrees to 75.6 degrees (C). Table 5 shows the qualitative and quantitative composition of the natural alcohols mixture obtained by this procedure.

TABLE 5

| Alcohol | Percent by Weight in the Mixture |
| --- | --- |
| 1-tetracosanol | 3.41 |
| 1-hexacosanol | 9.31 |
| 1-heptacosanol | 1.82 |
| 1-octacosanol | 38.31 |
| 1-nonacosanol | 3.45 |
| 1-triacontanol | 20.03 |
| 1-dotriacontanol | 16.19 |
| 1-tetratriacontanol | 3.41 |

EXAMPLE 3

The extraction process is performed using 300 liters of heptane as solvent for 14 hours on 5 kg of beeswax. The product obtained is cooled at temperatures between 3 degrees C. and 8 degrees C., whereby it is recrystallized using benzene. The natural alcohols mixture (1590 g) is obtained with a purity of 97.45%. The melting point of the mixture ranges between 73.3 degrees and 76.3 degrees C.

Table 6 shows the qualitative and quantitative composition of the natural alcohols mixture obtained by this procedure.

TABLE 6

| Alcohol | Percent by Weight in the Mixture |
| --- | --- |
| 1-tetracosanol | 3.50 |
| 1-hexacosanol | 9.63 |
| 1-heptacosanol | 1.90 |
| 1-octacosanol | 38.39 |
| 1-nonacosanol | 3.52 |
| 1-triacontanol | 20.98 |
| 1-dotriacontanol | 16.11 |
| 1-tetratriacontanol | 3.42 |

EXAMPLE 4 b 15kg of solid (beeswax) was subjected to solid-liquid extraction using toluene as solvent in a conventional solid-liquid extractor with a solid to liquid ratio of 1 to 80 for 12 hours. The extract was recovered and recrystallized using methanol, ethanol (1:1) as solvent in a temperature range of 2 degrees C. to 10 degrees C. This procedure resulted in recovery of 4.95 kg of recrystallized alcohol mixture with a purity of 97.05%. The melting point of the mixture ranges between 73.6 degrees and 77.1 degrees C. Table 7 shows the qualitative and quantitative composition ofthe natural alcohols mixture obtained using this procedure.

TABLE 7

| Alcohol | Percent by Weight in the Mixture |
| --- | --- |
| 1-tetracosanol | 3.42 |
| 1-hexacosanol | 9.42 |
| 1-heptacosanol | 1.95 |
| 1-octacosanol | 39.30 |
| 1-nonacosanol | 3.48 |
| 1-triacontanol | 19.92 |

TABLE 7-continued

| Alcohol | Percent by Weight in the Mixture |
| --- | --- |
| 1-dotriacontanol | 16.12 |
| 1-tetratriacontanol | 3.44 |

EXAMPLE 5

35 kg of solid (beeswax) was extracted in a Soxhlet extractor using 1750 liters of trichloroethylene as solvent for 12 hours. After that, the extracted material was cooled at temperatures ranging from 5 degrees C. to 15 degrees C. and recovered. The recovered extract was recrystallized using methyl ethyl ketone as solvent. This procedure resulted in a recovery of 10.85 kg of recrystallized product having a purity of 97.09%. The melting point of the recrystallized natural alcohol mixture ranges between 72.8 degrees and 75.9 degrees C. Table 8 shows the qualitative and quantitative composition of the natural alcohols mixture obtained using this procedure.

TABLE 8

| Alcohol | Percent by Weight in the Mixture |
| --- | --- |
| 1-tetracosanol | 3.42 |
| 1-hexacosanol | 9.39 |
| 1-heptacosanol | 1.84 |
| 1-octacosanol | 38.86 |
| 1-nonacosanol | 3.41 |
| 1-triacontanol | 20.12 |
| 1-dotriacontanol | 16.59 |
| 1-tetratriacontanol | 3.46 |

EXAMPLE 6

50 kg of solid (beeswax) was extracted in a conventional solid-liquid extraction system at a solid to liquid ratio of 1 to 80 for 6 hours using dichloroethane as solvent. The extract obtained was cooled at a temperature range from 5 degrees C. to 15 degrees C. A solid extract was then recovered and recrystallized using toluene as solvent in a temperature range of 2 degrees C. to 10 degrees C. The recrystallized alcohol mixture which was obtained (16.75 kg) had a purity of 96.08%. The melting point of the recrystallized natural alcohol mixture obtained in this procedure ranges between 72.1 degrees and 74.7 degrees C. Table 9 shows the qualitative and quantitative composition of the natural alcohols mixture obtained using this procedure.

TABLE 9

| Alcohol | Percent by Weight in the Mixture |
| --- | --- |
| 1-tetracosanol | 3.41 |
| 1-hexacosanol | 9.38 |
| 1-heptacosanol | 1.80 |
| 1-octacosanol | 38.65 |
| 1-nonacosanol | 3.40 |
| 1-triacontanol | 19.91 |
| 1-dotriacontanol | 16.13 |
| 1-tetratriacontanol | 3.40 |

EXAMPLE 7

75 kg of solid (beeswax) was subjected to solid-liquid extraction using benzene as solvent in a conventional solid-liquid extractor with a solid to liquid ratio of 1 to 50 for 8 hours. After that the extract was cooled at a temperature from 2° C. to 10° C. and then it was crystallized using toluene as solvent. This procedure resulted in recovery of 24.6 kg of recrystallized alcohol mixture with a purity of 96.36%. The melting point of the natural alcohol mixture obtained by this procedure ranges between 73.1 and 76.8° C. Table 10° shows the qualitative and quantitative composition of the natural alcohols mixture obtained using this procedure.

TABLE 10

| Natural Mixture | Percent by Weight in the Mixture |
| --- | --- |
| 1-tetracosanol | 3.42 |
| 1-hexacosanol | 9.33 |
| 1-heptacosanol | 1.83 |
| 1-octacosanol | 38.51 |
| 1-nonacosanol | 3.45 |
| 1-triacontanol | 20.21 |
| 1-dotriacontanol | 16.16 |
| 1-tetratriacontanol | 3.45 |

EXAMPLE 8

Male New Zealand rabbits (2–3 kg) were adapted to laboratory conditions for 15 days and randomly distributed in 4 groups. The first group (control) received only vehicle orally. The second, third and fourth groups received oral doses of BMHPAA in the amount of 5, 50 and 200 mg/kg respectively suspended in an Acacia gum/water vehicle by gastric gavage (1 ml/kg) for 4 weeks. Lipid profile was determined at baseline (the day before starting the treatment and 4 weeks after. BMHPAA administered orally at 5, 50 and 200 mg/kg during 30 days significantly reduced (Wilcoxon $p<0.05$) in a dose-dependent manner total cholesterol and LDL-serum levels. Moreover, the percent changes in control and treated groups were statistically different (Mann Whitney U, $p<0.05$). In this experimental series, the highest dose of BMHPAA administered (200 mg/kg) reduced serum cholesterol and LDL-C by 51 and 78%.

EXAMPLE 9

Male New Zealand rabbits were distributed randomly in 4 groups: a control group (only receiving vehicle by gastric gavage) and 3 groups, the individuals of which were dosed with the alcohol mixture of the invention, octacosanol and hexacosanol, respectively at 5 mg/kg. Serum lipid profile was determined at base line and 30 days before treatment. The alcohol mixture of the invention decreased significantly total cholesterol and LDL-C. Moreover, levels of cholesterol, LDL-C and triglycerides of rabbits treated with the mixture of the invention were significantly lower than those of the controls. Nevertheless, the changes on serum lipid profile which occurred in groups treated with octacosanol or hexacosanol did not achieve statistical significance as is shown in Table 11.

TABLE 11

| Group | Dose (mg/kg) | Baseline | After Treatment |
| --- | --- | --- | --- |
| Total Cholesterol | | | |
| Controls | 0 | 2.5 | 2.3 |
| BMHPAA | 5 | 2.8 | 1.6*+ |
| Octacosanol | 5 | 2.7 | 2.2 |
| Hexacosanol | 5 | 2.6 | 2.4 |
| LDL-C | | | |
| Control | 0 | 1.5 | 1.2 |
| BMHPAA | 5 | 1.3 | 0.6*+ |
| Octacosonal | 5 | 1.4 | 0.9 |
| Hexacosanol | 5 | 1.5 | 1.0 |
| Triglycerides | | | |
| Control | 0 | 0.80 | 0.82 |
| BMHPAA | 5 | 0.78 | 0.55* |
| Octacosanol | 5 | 0.77 | 0.70 |
| Hexacosanol | 5 | 0.80 | 0.78 |

*$p < 0.05$ comparison with controls (Mann Whitney U test)
+$p < 0.05$ comparison with baseline (Wilcoxon)

EXAMPLE 10

After 5 weeks of diet-only period, forty-five outpatients in whom cholesterol and LDL-C values were not controlled by diet received 5 mg of the alcohol mixture of the invention (twice-a-day at lunch and dinner) or placebo for 6 weeks. During this active treatment period, dietary conditions were maintained. Lipid profile levels were determined at baseline (end of the diet-only period) as well as 4 and 6 weeks after therapy. The alcohol mixture of the invention (BMHPAA) reduced significantly total serum cholesterol by 16.23% and LDL-C by 21.33%. Also cholesterol to HDL-C and LDL-C to HDL-C ratios were significantly reduced to 17.67% and 22.28%, respectively ($p<0.05$ Wilcoxon test for paired data). In all patients levels of both total cholesterol and LDL-C were lower 6 weeks after treatment than at baseline. Changes on other lipid profile fractions were non significant. Results are shown in Tables 12 and 13. Table 12 shows the effects of BMHPAA (10 mg/per day, 5 mg twice a day) on serum lipid profile (mmol/L) in patients with Type II hyperlipoproteinemia

TABLE 12

| | n | Baseline (X + SD) | week 6 (X + SD) |
| --- | --- | --- | --- |
| Total Cholesterol | | | |
| BMHPAA | 22 | 7.43 + 1.29 | 6.21 + 1.38***'" |
| Placebo | 23 | 6.97 + 0.72 | 6.70 + 0.75* |
| LDL-C | | | |
| BMHPAA | 22 | 5.54 + 1.22 | 4.35 + 1.31.sup.a |
| Placebo | 23 | 5.07 + 0.63 | 4.97 + 0.67 |
| HDL-C | | | |
| BMHPAA | 22 | 1.03 + 0.26 | 1.10 + 0.28 |
| Placebo | 23 | 2.03 + 0.64 | 1.87 + 0.67 |
| VLDLC | | | |
| BMHPAA | 22 | 1.09 + 0.43 | 0.79 + 0.40 |
| Placebo | 23 | 0.92 + 0.29 | 0.85 + 0.31 |

X = median value
SD = standard deviation
n 32 number of patients

TABLE 12-continued

|   | n | Baseline (X + SD) | week 6 (X + SD) |
|---|---|---|---|

*p < 0.01; ***p < 0.0001 comparison with baseline (Wilcoxon)
sup. a p < 0.05 comparison with placebo, absolute values, Mann Whitney U test
""p < 0.0001 comparison with placebo (Mann Whitney U test)
""""p < 0.00001 comparison with placebo (Mann Whitney U test)

TABLE 13

Effects of BMHPAA (10 mg/day, 5 mg twice-a-day) on serum lipid ratios (mmol/L) in patients with Type II hyperliproteinemia.

|   | n | Baseline (X + SD) | week 6 (X + SD) |
|---|---|---|---|
| LDL-C to HDL-C | | | |
| BMHPAA | 22 | 5.71 + 1.82 | 4.18 + 1.59**"".sup a |
| Placebo | 23 | 4.92 + 1.85 | 5.30 + 1.79 |
| Cholesterol to HDL-C | | | |
| BMHPAA | 22 | 7.65 + 2.18 | 5.94 + 1.81*" |
| Placebo | 23 | 6.69 + 2.21 | 7.06 + 2.05 | n = number of patients
X = median value
SD = standard deviation
*p < 0.05; **p < 0.01 comparison with baseline (Wilcoxon)
.sup. a p < 0.05 comparison with placebo, absolute values, Mann Whitney U test
"p < 0.05 comparison with placebo (Mann Whitney U test)
""p < 0.01 comparison with placebo (Mann Whitney U test)

EXAMPLE 11

A group of patients with Type II hyperliproteinemia received 15 mg of the BMHPAA formulation administered orally after 8 weeks of diet only period (baseline). Lipid profile was determined at baseline and 8 weeks after therapy. The main results are summarized in table 14. Formulation with BMHPAA significantly reduced serum total cholesterol by 16.44% and LDL-C by 23.51%.

Type II hyperliproteinemia, wherein the changes of cholesterol LDL-C and HDL-C are indicated mean values and the change of triglycerides as median value are shown in Table 15. HDL-C raised 6.40%, while triglycerides and VLDL-C decreased 7.80% and 10.83%, respectively but these changes were not statistically significant. Table 15 also shows that the LDL-C to HDL-C and cholesterol to HDL-C ratios decreased significantly by 29.07% and 23.72%, respectively.

TABLE 14

Effects of BMHPAA on serum lipids profile and lipoprotein in patient with Type II hyperliproteinemia.

| Parameters | n | Baseline (X + SD) | n | week 8 (X + SD) |
|---|---|---|---|---|
| Cholesterol | 25 | 7.84 + 1.14 | 25 | 6.50 + 1.21**** |
| LDL-C | 17 | 5.86 + 1.11 | 18 | 4.33 + 1.32** |
| HDL-C | 19 | 1.03 + 0.44 | 20 | 2.30 + 1.42 |
| Triglycerides | 19 | 2.30 + 1.42 | 20 | 2.14 + 1.06 |
| VLDL-C | 19 | 1.05 + 0.64 | 20 | 0.97 + 0.48 | n = number of patients
X = median value
SD = standard deviation
p < 0.01, **p < 0.0001 (Wilcoxon test)

TABLE 15

Effects of BMHPAA on LDL-C to HDL-C and cholesterol to HDL-C ratios in patients with Type II hyperliproteinemia.

| Ratio Measured | n | Ratio at Baseline (X + SD) | n | Ratio at week 8 (X + SD) |
|---|---|---|---|---|
| LDL-C to HDL-C | 17 | 6.34 + 2.79 | 18 | 3.82 + 1.55** |
| Cholesterol to HDL-C | 19 | 8.83 + 3.49 | 20 | 6.07 + 2.17** | n = number of patients
X = median value
SD = standard deviation
**p < 0.01 (Wilcoxon test)

EXAMPLE 12

BMHPAA and its effect on adenosine diphosphate (ADP) and collagen-induced platelet aggregation in rats were investigated. A group of male Sprague Dawley rats weighing 250 to 350 g were distributed randomly between 2 experimental groups. BMHPAA was administered orally formulated as a suspension in an Acacia gum-water vehicle by gavage for 4 weeks. The following groups were included: Control group (only receiving vehicle) and a BMHPAA (25 mg/kg) treated group. To conduct the platelet aggregation assay, rats were anaesthetized in an ether atmosphere. Abdomens were opened and blood (5 mL) was drawn from the vena cava and mixed with 3.8% sodium citrate (1 volume citrate per 9 or blood). Platelet-rich plasma (PRP) was obtained by blood centrifugation. Platelet-poor plasma (PPP) was obtained by PRP aliquot centrifugation 330×g for 15 minutes. Platelet aggregation was induced by ADP and by collagen and measured with a Payton aggregometer as described by L. McGregor, R. Morazain and S. Renaud, 1980; Effect of dietary lineolic acid on platelet functions in the rat; Thrombosis Res 20, 4099. The statistical comparison of results between treatment and control groups was carried out using the non parametric Mann-Whitney U test. Rats treated with BMHPAA at 25 mg/kg for 4 weeks showed a significant inhibition of platelet aggregation ex vivo when submaximum ADP and collagen doses were administered.

EXAMPLE 13

To characterize the effect of BMHPAA on ex vivo platelet aggregation in rats, some studies of the time course of its platelet antiaggregatory effects were done. For that purpose, Sprague-Dawley rats of both sexes weighing 250 to 350 g were distributed in 4 experimental groups: one control group and 3 groups treated with single doses of BMHPAA at 25, 50 and 200 mg/kg, respectively. Moreover, after 2, 6 and 24 hours of administering the 200 mg/kg dose, the effects on platelet aggregation were investigated.

BMHPAA was formulated in a suspension as described in Example 12 and administered orally as single doses, two hours prior to the experiment. Control animals received the same dosage volume which contained only vehicle. All animals were deprived of food, but had free access to water for 20 hours prior to the experiment. All animals were anesthetized with ether and blood samples were drawn from the vena cava and mixed with 3.8% sodium citrate (9 volumes of blood per 1 of anticoagulant). Blood was centrifuged at 250 g for 10 minutes to obtain platelet-rich plasma (PRP). Once PRP was isolated, the rest was centrifuged at 1300 g for 15 minutes to obtain platelet-poor plasma (PPP).

Platelet aggregation was quantified by turbidimetric method as described by Borbn G., 1962; Aggregation of blood platelets by adenosine diphosphate and its reversal, Nature (London) 194, 927–929. Platelet aggregation levels were measured after calibrating the equipment at 0% of light transmission for PRP and at 100% for PPP.

BMHPAA (50 and 200 mg/kg) administered 2 hours before blood sampling inhibited ADP-induced platelet aggregation while lower doses (25 mg/kg) did not significantly responses to ADP. The highest dose of BMHPAA (200 mg/kg) was chosen to study time course of antiplatelet effects. Although, after 2 hours platelet aggregation was significantly inhibited, after 6 hours the inhibition was only marginally significant (p=0.06), while after 24 hours no statistical significance was obtained. Results show that oral administration of BMHPAA to rats two hours prior to blood sampling inhibited dose-dependently ADP-induces platelet aggregation in PRP of rats treated with BMHPAA at 50 and 200 mg/kg.

The inhibitory effect of BMHPAA on ADP-induced aggregation is reversible, since 6 hours after treatment with it at 200 mg/kg, inhibition of platelet aggregation was only marginally significant, and 24 hours after treatment a lack of effectiveness was appreciated, showing that BMHPAA does not induce permanent cell modifications.

EXAMPLE 14

The effects of BMHPAA on "in vivo" intravascular platelet aggregation in rats and on collagen-induced mortality in mice were studied. Male Sprague Dawley rats weighing 250 to 300 g and 57BL6 female mice weighing 20 to 25 g were distributed randomly among different experimental groups. BMHPAA was formulated into a suspension as described in Example 12, while acetyl salicyclic acid (ASA) was dissolved in 5% $NaHCO_3$. Drugs were administered orally by gavage 2 hours before the assay. Animals received no food for 16 hours prior to oral administration of the drugs. Rats were given 1 ml/100 g body weight and mice 0.5 ml/20 g bodyweight while control animals received equivalent dosage volumes which contained only vehicle. Four experimental groups were used in the study of the intravascular platelet aggregation in rats: 1) Controls, 2, 3 and 4 (BMHPAA) at 5, 10 and 20 mg/kg. Animals were anaesthetized i.p. with pentobarbital sodium (10–40 mg/kg). A cannula was inserted into a carotid artery for blood sampling before and 90 seconds after a 30 mg/kg collagen i.v. injection into the penile vein.

900 microliters (mu L) of blood was collected in plastic tubes containing a 100 mu L mixture with 0.7 mg/mL indomethacin and 19 mg/mL EDTA. An aliquote was used to determine platelet concentration in each sample through optic microscopic counting. Blood was then centrifuged and plasma malondialdehyde (MDA) concentration was quantified through the thiobarbituric acid method (M. Satoh, 1978, Serum lipid peroxide in cerebrovascular disorders determined by anew calorimetric method; Clin.Chim Acts 90,34–43). Platelet count and plasma MDA concentration variations after injecting collagen were expressed as a percent ofbaseline values. Differences between control and treatment groups were determined using the Mann-Whitney U Test. For the study of the collagen induced mortality in rats, the experimental groups were the following: 1) controls: animals only receiving the vehicle, but inducing mortality by a collagen intravenous inj ection, 2) Animals pretreated with BMHPAA at 360 mg/kg 2 hours prior collagen injection; 3) Animals retreated with BMHPAA at 360 mg/kg 1,4,8 and 24 hours prior to mortality induction; and 4) Animals retreated with BMHPAA at 180 mg/kg and ASA at 50 mg/kg 2 hours prior to the assay.

Acid-soluble veal skin collagen type III was prepared as described by Kimura et al. (Y. Kimura, T. Kaube and K. Watanabe, 1985; Effect of celostagel on platelet aggregation and experimental thrombosis; Arzneim Forsch Drug Res. 35, 114–1148) and used at final concentration of 2.5 mg/ml. A 0.1 ml/20 g injection was administered via the tetro-orbital plexus. This dose caused from 60 to 100% mortality in control animals. The comparison of the mortality percent between control and treatment animals was done using Fisher's Exact probability Test.

BMHPAA significantly inhibited the decrease in circulating platelet count and the simultaneous increase of MDA concentration in plasma induced by collagen. Collagen-induced mortality was significantly reduced by BMHPAA at 360 mg/kg. This protective effect on the collagen induced mortality was observed when this dose was administered 1 and 4 hours prior to the assay, but significance was not obtained when administered 8 hours before the assay.

The combination of BMHPAA and ASA that were ineffective when administered independently were obviously protective when administered together, thus indicating a synergism between BMHPAA and ASA antithrombotic effects.

EXAMPLE 15

For the analysis of the effect that BMHPAA has on rat cerebral infarction, male Sprague Dawleyrats weighing 290 to 330 g were distributed into the following experimental groups: 1) negative control: non-ligatedrats receiving onlythe vehicle by gastric gavage, 2) positive control: ligated rats also receiving only the vehicle by gastric gavage, 3) and 4): ligated rats receiving BMHPAA (5 and 25 mg/kg respectively) by the same route. The different treatments were administered daily for 4 weeks. The last one was administered 12 hours before ligation, as well as 8 and 24 hours after the ligation, as commonly used in this model.

For the induction of cerebral ischemia, animals were gently anaesthetized and oligemia was produced by bilateral ligation of the common carotid arteries. a Immediately after, sodiumnitroprusside (0.8 mg/250 g) was injected subcutaneously to induce arterial hypertension. Carotid clamps were removed 60 minutes after and animals were observed for 72 hours and then sacrificed. Brains were rapidly removed and placed in an oven at 80° C. for 24 hours. Both wet and dry weight were measured to determine the water content (edema). The statistical analysis of the results was carried out using the non-parametric Mann-Whitney U test. BMHPAA at 25 mg/kg decreased significantly the cerebral edema (p<<0.05) when administered daily for 4 weeks. This dose also reduced mortality rates and percent of animals with edema, although these other reductions did not reach significant levels. These findings show that BMHPAA at 25 mg/kg significantly protect cerebral ischemia experimentally induced in rats, since a significant reduction in the brain edema was produced. There was also a reduction in the percent of animals treated showing brain edema areas, but this reduction did not reach significant levels.

EXAMPLE 16

To study the synergism between BMHPAA and aspirin on brain ischemia induced in rats, male Sprague Dawley rats weighing 250 to 300 g were distributed in 5 groups: 1) negative control (non ligated rats); 2) positive control (ligated animals receiving only the vehicle); 3) animals orally receiving by gavage 25 mg/kg of BMHPAA; 4) animals orally receiving ASA dissolved in 5% sodium bicarbonate (30 mg/kg); 5) rats orally administered ASA (30 mg/kg)+BMHPAA (25 mg/kg). Treatments were administered 2 hours prior the experiment.

For the ischemia induction, animals were gently anaesthetized with ether and common arteries were dissected and ligated. Hypotension was then induced by a subcutaneous injection of sodium nitroprusside (0.8 mg/250 g). After 60 min. the carotid clamps were removed and the animals were then observed for 24 hours. They were then sacrificed and the brains were removed immediately and placed in an oven at 80° C. for 24 hours to determine water content. Results were analyzed using the non parametric Mann-Whitney U test. Neither BMHPAA nor aspirin significantly reduced brain ischemia when they were separately administered to animals at the aforementioned doses. Nevertheless, when administered together a significant protection was obtained. These results confirm a synergism between antischemic effect of BMHPAA and ASA.

EXAMPLE 17

Mongolian gerbils of both sexes (60–80 g body weight) were used and adapted previously to laboratory conditions for a week. BMHPAA was administered by gastric gavage suspended in a Tween 20-water vehicle. Animals were distributed randomly into the following groups: (1) positive control (ligated animals, only receiving the vehicle), (2) BMHPAA (50 mg/kg) and (3) BMHPAA 300 mg/kg). All treatments were administered two hours prior to induction of brain ischemia. The left common carotid artery was exposed in the neck and doubly ligated with surgical thread under ether anaesthesia. The behavior of each animal was observed for 24 hours while recording the clinical symptoms of brain ischemia such as circling, rolling fits and seizures. Mortality was also recorded, Statistical comparison of the frequency of mortality and clinical symptoms between groups were compared using the Fisher's Exact probability test.

Results show that treatment decrease symptoms and significantly reduced mortality.

It is well known that approximately 60% of Mongolian gerbils develop neurological deficits, such as circling behavior and rolling fits after ligation of the common carotid artery. These symptoms have been associated with the fact that in approximately $2/3$ of these animals there is an incompleteness or absence of connecting arteries between the basilar and carotid system. Moreover, almost 80% of the animals showing clinical symptoms die within 72 hours after ligation.

Since the severity of cerebral infarction of all brain regions is difficult to assess, while mortality rate is easy to quantify, this parameter has been used commonly for evaluating putative anti-ischemic drugs. Our results show that BMHPAA (200 mg/kg) significantly protects the brain global ischemia induced by unilateral ligation of common artery in Mongolian gerbils, thus, indicating usefulness of BMHPAA for the prevention of global ischemia development.

EXAMPLE 18

Sprague Dawley rats of both sexes, weighing 200 to 220 g were used to test the effects of BMHPAA on gastric ulcer induced by different drugs. The animals were adapted to laboratory conditions for a week with water and food ad libitum. After a 24 hour period of fasting, the rats were divided randomly into two experimental groups. The first group was intra peritoneally injected with BMHPAA at 25 mg/kg suspended in a Tween 20/water vehicle, while the second group (control) only received the same volume of vehicle. In each case, experimental procedure for induction of different types of drug-induced gastric ulcer was performed in both control and treated groups (two groups were used for each type of ulcer):

A) Gastric Ulcer Experimentally Induced by C4880(Sigma)

The procedure used was similar to that described by F. Awouters, C. J. E. Nemegeens and P. A. J. Jansken (1985: A pharmacological analysis of the rat mast cell 5-HT gastric lesion test and the effect of ketanserin; Drug Div. Res. 5, 303–312.). For that, diphenhydramine was injected subcutaneously at 10 mg/kg and 30 min later C4880 was injected intravenously. Animals were sacrificed 4 hours after C4880 administration and stomachs were removed quickly, opened lengthwise along the greater curvature and washed with distilled water. Then, mucosas were exposed and the damaged area was measured by means of a magnifying glass. Results were expressed as percent of area showing damage. In this model, pretreatments with BMHPAA or vehicle were administered 30 minutes before diphenhydramine injection.

B) Ulcer Induced by Alcohol

The procedure was performed as described by H. Zengil, E. Onik, T. S. Erean and R. K. Tarker (1987: Protective Effect of Ilopnost and UK 38485 against gastric mucosal damage by various stimuli, Prostaglandins Leukotrienes and Medicine 30, 61–67). For that reason, one hour after dosing with BMHPAA or vehicle, rats were administered orally by gastric gavage ethanol 40% (ml/rat). Two hours later, rats were sacrificed and the procedure for quantifying gas gastric ulcer was performed as described by Zengil et al.

C) Gastric Ulcer Induced by ASA

The procedure was performed according to the same authors referred in the previous paragraph. 100 mg/kg of ASA was orally administered to rats one hour after treatment with BMHPAA or vehicle. Two hours later, the rats were sacrificed and the procedure for gastric ulcer measurement was done as described. Comparisons between control and BMHPAA treated groups were performed using the non parametric Mann-Whitney U test. BMHPAA administered intra peritoneally (25 mg/kg) inhibited significantly the occurrence of gastric ulcer induced by C4880, ethanol and ASA. Moreover, as can be observed in Table 16, BMHPAA administered orally not only reduced $TxB_2$ but also increases $PgI_2$, thus very significantly reducing $TxB_2$ to $PGI_2$ ratio.

TABLE 16

Effect of BMHPAA and ASA on the $TxB_2$ levels and 6 keto PgFla in mice serum

| Group | $TxB_2$ (ng/mL) | 6 ketoPgFla (ng/mL) | Index $TxB_2$ KetoPgFla |
|---|---|---|---|
| Control | 286 + 16.7 | 1.65 + 0.26 | 173 |
| ASA | 36.3 + 13.3**(a) | 1.12 + 0.41 | 46.5 |
| BMHPAA 50 mg/Kg | 182 + 31.9**(b) | 3.91 + 0.4* | 32.4 |
| BMHPAA 180 mg/Kg | 9.25 + 5.4**(c) | 1.57 + 0.16 | 5.8 |

*p < 0.05; p < 0.01, *p < 0.001
(a)(b)(c) = (Mann Whitney U test)
The inhibition of the $TxB_2$ levels and the increase of $PgI_2$ induced by BMHPAA could explain the protective effect of this mixture against gastric ulcer. Thus, it is observed a highly significant decrease of the $TxB_2$ to $PgI_2$ ratio when combined treatment of BMHPAA and ASA is used. Moreover, this mechanism also could support alcohols mixture effects on the other drug-induced gastric ulcer.

EXAMPLE 19

Forty-five outpatients from both sexes, aged from 25 to 70 years, with Type II hyperlipoproteinemia received, under double blind conditions, BMHPAA or placebo once a day for 6 weeks (treated patients received BMHPAA at 5 mg/day). Before and after treatment the following parameters were investigated: bleeding time, platelet count, prothrombin time, antithrombin III activity, lysis time, plasmatic euglobulin fraction, platelet aggregation induced by ADP and malondialdehyde (MDA) concentration.

Table 17 summarizes the data obtained in this example. The data show that none of the parameters related to the coagulation process were affected, while a significant difference between group ofplatelet aggregation-ADP induced was obtained. In addition, a marginally significant reduction of MDA was also observed (p=0.058).

TABLE 17

Effects of BMHPAA treatment in blood coagulation and platelet aggregation in patients with Type II hyperlipo-proteinemia.

| | Time of Analysis | Placebo | BMHPAA (5 mg/day) |
|---|---|---|---|
| Bleeding time | 0 | 2'47" +/− 1'26" | 2'31" +/− 1'24" |
| | 6w | 2'10" +/− 1'34" | 2'08" +/− 1'06" |
| Platelet count | 0 | 201.23 +/− 29.98 | 198.13 +/− 39.48 |
| | 6w | 188.55 +/− 35.99 | 175.33 +/− 40.87 |
| Prothrombin time | 0 | 13.67 +/− 1.80 | 14.43 +/− 4.18 |
| | 6w | 13.40 +/− 1.10 | 13.69 +/− 2.25 |
| Fibrinogen | 0 | 2.64 +/− 0.46 | 2.84 +/− 0.54 |
| | 6w | 2.81 +/− 0.52 | 2.92 +/− 0.44 | w = weeks

While the present invention has been described in terms of certain preferred embodiments, one skilled in the art will readily appreciate that various modifications, changes, omissions and substitutions may be made without departing from the spirit thereof. It is intended, therefore, that the present invention be limited solely by the scope of the following claims.

I claim:

1. A method for isolating a mixture of primary aliphatic alcohols from non-alcoholic compounds contained in natural wax wherein said method comprises subjecting unsaponified beeswax to liquid extraction with a liquid organic extractant in which said alcohols are soluble; recovering said alcohol mixture from said extractant whereby said alcohol mixture is isolated from said nonalcoholic compounds contained in said beeswax and said isolated alcohol mixture includes:

1–4 wt. % of 1-tetracosanol
   7–12 wt. % of 1-hexacosanol
   1–4 wt. % of 1-heptacosanol
   30–60 wt. % of 1-octacosanol
   2–5 wt. % of 1-nonacosanol
   16–26 wt. % of 1-triacontanol
   13–22 wt. % of 1-dotriacontanol
   2–6 wt. % 1-tetratriacontanol.

2. The method of claim 1 wherein said liquid organic extractant is selected from the group consisting of acetone, toluene, benzene, ethanol, heptane, methanol, phenol, ether, trichloroethane, methyl ethyl ketone, butanol, 1,2 dichloroethane, dichloromethane, chloroform and mixtures thereof; and said isolated alcohol mixture has a purity level of 93–97% with respect to said nonalcoholic compounds contained in said beeswax and said isolated alcohol mixture includes:

2–4 wt. % of 1-tetracosanol
   9–10 wt. % of 1-hexacosanol
   2–3 wt. % of 1-heptacosanol
   35–40 wt. % of 1-octacosanol
   3–4 wt. % of 1-nonacosanol
   19–22 wt. % of 1-triacontanol
   15–20 wt. % of 1-dotriacontanol
   3–4 wt. % 1-tetratriacontanol.

3. The method of claim 2 wherein said beeswax is selected to have the following characteristics:
   Melting point: 61–65° C.
   Cloudpoint: <65° C.
   Flash point: 242–250° C.
   Specific gravity @25C: 0.950–0.960
   Saponification value: 88–102
   Resin value: 1–2
   Oil value: 2–6
   Acid value: 17–24
   Ester value: 72–79
   Ester—acid ratio: 3.3–4.2
   Free alcohol value: 3–10
and said purity level is 97–99% and said isolated alcohol mixture includes:
   3.5±0.1 wt. % of 1-tetracosanol
   9.5±0.2 wt. % of 1-hexacosanol
   2.0±0.2 wt. % of 1-heptacosanol
   38.5±1.2 wt. % of 1-octacosanol
   3.5±0.1 wt. % of 1-nonacosanol
   20.5±0.6 wt. % of 1-triacontanol
   16.5±0.4 wt. % of 1-dotriacontanol
   3.5±0.1 wt. % 1-tetratriacontanol.

4. A mixture of primary aliphatic alcohols isolated from beeswax; said mixture containing:
   1–4 wt. % of 1-tetracosanol
   7–12 wt. % of 1-hexacosanol
   1–4 wt. % of 1-heptacosanol
   30–60 wt. % of 1-octacosanol
   2–5 wt. % of 1-nonacosanol
   16–26 wt. % of 1-triacontanol
   13–22 wt. % of 1-dotriacontanol
   2–6 wt. % 1-tetratriacontanol.

5. The mixture of claim 4 which contains:
   2–4 wt. % of 1-tetracosanol
   9–10 wt. % of 1-hexacosanol
   2–3 wt. % of 1-heptacosanol
   35–40 wt. % of 1-octacosanol
   3–4 wt. % of 1-nonacosanol
   19–22 wt. % of 1-triacontanol
   15–20 wt. % of 1-dotriacontanol
   3–4 wt. % 1-tetratriacontanol.

6. The mixture of claim 5 which contains:
   3.5±0.1 wt. % of 1-tetracosanol
   9.5±0.2 wt. % of 1-hexacosanol
   2.0±0.2 wt. % of 1-heptacosanol
   38.5±1.2 wt. % of 1-octacosanol
   3.5±0.1 wt. % of 1-nonacosanol
   20.5±0.6 wt. % of 1-triacontanol
   16.5±0.4 wt. % of 1-dotriacontanol
   3.5±0.1 wt. % 1-tetratriacontanol.

7. A pharmaceutical composition which comprises the mixture of claim 4 in combination with a pharmaceutically acceptable carrier, excipient or dilutant.

8. A pharmaceutical composition which comprises the mixture of claim 5 in combination with a pharmaceutically acceptable carrier, excipient or dilutant.

9. A pharmaceutical composition which comprises the mixture of claim 6 in combination with a pharmaceutically acceptable carrier, excipient or dilutant.

10. The composition of claim 7 in the form of a capsule, tablet, liquid or powder.

11. The composition of claim 8 in the form of a capsule, tablet, liquid or powder.

12. The composition of claim 9 in the form of a capsule, tablet, liquid or powder.

13. A method for treating or preventing hypercholesterolemia related diseases which comprises administering a pharmaceutically effective amount of the mixture of claim 4 to a human or mammal.

14. A method for treating or preventing hypercholesterolemia related diseases which comprises administering a pharmaceutically effective amount of the mixture of claim 5 to a human or mammal.

15. A method for treating or preventing hypercholesterolemia related diseases which comprises administering a pharmaceutically effective amount of the mixture of claim 6 to a human or mammal.

16. A method for reducing total cholesterol and LDL-C levels which comprises administering a pharmaceutically effective amount of the mixture according to claim 4 to a human or mammal in need thereof whereby said mixture inhibits cholesterol synthesis in the liver in the steps prior to mevalonate formation and increases the LDL catabolic rate which thereby increases hepatic LDL receptor activity.

17. A method of using the mixture of claim 4 which comprises administering said mixture as an antiplatelet, anti-inflammatory, anti-thrombotic or anti-ischemic agent to an individual in need thereof.

18. A method for preventing neurodegenerative disorders which comprises administering the mixture of claim 4 in a pharmaceutically acceptable amount to an individual in need thereof.

19. A method for improving male sexual activity which comprises administering the mixture of claim 4 to an individual in need thereof.

* * * * *